(12) United States Patent
Franke

(10) Patent No.: US 11,027,266 B2
(45) Date of Patent: Jun. 8, 2021

(54) PHOSPHOROUS ACID P,P'-[5,5',6,6'-TETRAMETHYL-3,3'-BIS(L-METHYLETHYL)[1,1'-BIPHENYL]-2,2'-DIYL] P,P,P',P'-TETRAKIS(2,4-DIMETHYLPHENYL) ESTER IN HYDROFORMYLATION

(71) Applicant: EVONIK DEGUSSA GMBH, Essen (DE)

(72) Inventor: Robert Franke, Marl (DE)

(73) Assignee: EVONIK OPERATIONS GMBH, Essen (DE)

( * ) Notice: Subject to any disclaimer, the term of this patent is extended or adjusted under 35 U.S.C. 154(b) by 137 days.

(21) Appl. No.: 15/805,372

(22) Filed: Nov. 7, 2017

(65) Prior Publication Data

US 2018/0126366 A1    May 10, 2018

(30) Foreign Application Priority Data

Nov. 8, 2016 (EP) .................................... 16197717

(51) Int. Cl.
| | |
|---|---|
| *B01J 31/02* | (2006.01) |
| *C07F 15/00* | (2006.01) |
| *C07C 45/50* | (2006.01) |
| *B01J 31/28* | (2006.01) |
| *C07C 45/62* | (2006.01) |
| *C07F 9/145* | (2006.01) |

(52) U.S. Cl.
CPC ............ *B01J 31/0259* (2013.01); *B01J 31/28* (2013.01); *C07C 45/505* (2013.01); *C07C 45/62* (2013.01); *C07F 9/145* (2013.01); *C07F 15/0006* (2013.01); *C07F 15/0073* (2013.01)

(58) Field of Classification Search
None
See application file for complete search history.

(56) References Cited

U.S. PATENT DOCUMENTS

| | | | |
|---|---|---|---|
| 4,769,498 A | 9/1988 | Billig et al. | |
| 5,723,641 A | 3/1998 | Tam et al. | |
| 5,910,600 A | 6/1999 | Urata et al. | |
| 6,069,267 A | 5/2000 | Tam | |
| 6,750,362 B2 | 6/2004 | Bunel et al. | |
| 7,087,797 B2 | 8/2006 | Sielcken et al. | |
| 7,629,484 B2 | 12/2009 | Ritter | |
| 7,935,850 B2 * | 5/2011 | Caers | C07C 2/66 568/451 |
| 9,650,401 B2 | 5/2017 | Dyballa et al. | |
| 9,676,805 B2 | 6/2017 | Dyballa et al. | |
| 2008/0015378 A1 * | 1/2008 | Foo | C07C 253/10 558/335 |
| 2013/0324756 A1 | 12/2013 | Kreider et al. | |
| 2015/0290633 A1 * | 10/2015 | Christiansen | B01J 31/0209 556/13 |
| 2016/0159839 A1 | 6/2016 | Dyballa et al. | |
| 2016/0159840 A1 | 6/2016 | Dyballa et al. | |
| 2016/0185685 A1 | 6/2016 | Dyballa et al. | |
| 2017/0129838 A1 | 5/2017 | Dyballa et al. | |
| 2017/0275316 A1 | 9/2017 | Dyballa et al. | |

FOREIGN PATENT DOCUMENTS

| | | | |
|---|---|---|---|
| CN | 1250053 A | 4/2000 | |
| CN | 1514818 A | 7/2004 | |
| CN | 1653038 A | 8/2005 | |
| CN | 101405292 A | 4/2009 | |
| CN | 105940006 A | 9/2016 | |
| DE | 10 2014 202500 A | 8/2015 | |
| EP | 2907819 A1 | 8/2015 | |
| JP | H10-045776 A | 2/1998 | |
| RU | 2584952 C1 | 5/2016 | |
| TW | 200740837 A | 11/2007 | |
| TW | 201422632 A | 6/2014 | |
| WO | 2007/109005 A2 | 9/2007 | |
| WO | 2012/095253 | 7/2012 | |
| WO | 2014/056733 | 4/2014 | |
| WO | WO 2014056733 * | 4/2014 | ............ C07F 9/6574 |
| WO | 2017/080690 A1 | 5/2017 | |

OTHER PUBLICATIONS

Search Report for Singapore Patent Application No. 10201709109Q dated May 15, 2018.
R. Franke, D. Selent, A. Börner, "Applied Hydroformylation", Chem. Rev. 2012, 112, pp. 5675-5732.
P. W. N. M. van Leeuwen, C. Claver, "Rhodium-catalyzed Hydroformylation", Kluwer Academic Publishers 2006, pp. 44-48.
U.S. Appl. No. 15/805,401, Dyballa et al., filed Nov. 7, 2017.
Korean Office Action for Application No. 20170147016 dated Mar. 7, 2019 (5 pages in Korean with English Translation).
Armarego, Wilfred L.F., et al. Purification of Laboratory Chemicals, Butterworth Heinemann (Elsevier), 6th edition, Oxford 2009 (index and chapter abstracts provided).

(Continued)

*Primary Examiner* — Yun Qian

(74) *Attorney, Agent, or Firm* — Smith, Gambrell & Russell, LLP

(57) ABSTRACT

The compound of the formula (1) and its complexes with metal cations are used for catalysis in hydroformylation processes.

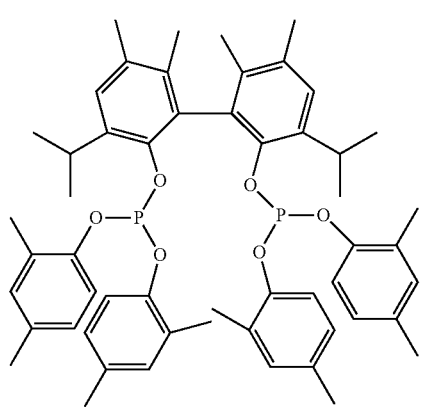

(1)

9 Claims, No Drawings

(56) References Cited

OTHER PUBLICATIONS

Harris, Robin K. et al. NMR Nomenclature, Nuclear Spin Properties and Conventions for Chemical Shifts. Pure Appl. Chem., 2001, vol. 73, pp. 1795-1818.
Harris, Robin K. et al. Further Conventions for NMR Shielding and Chemical Shifts. Pure Appl. Chem., 2008, vol. 80, pp. 59-84.
European Search Report dated Apr. 21, 2017 for EP 16 19 7717 (1 page).
Taiwan Search Report for Application No. 106138176 dated Feb. 18, 2019 (1 page).
Chinese Office Action for Application No. 201711083187.6 dated Jun. 27, 2019 (9 pages in Chinese with English Translation).
Chinese Search Report for Application No. 201711083187.6 dated Jun. 10, 2019 (2 pages in Chinese with English Translation).

* cited by examiner

PHOSPHOROUS ACID P,P'-[5,5',6,6'-TETRAMETHYL-3,3'-BIS(L-METHYLETHYL)[1,1'-BIPHENYL]-2,2'-DIYL] P,P,P',P'-TETRAKIS(2,4-DIMETHYLPHENYL) ESTER IN HYDROFORMYLATION

The invention relates to the preparation of phosphorous acid P,P'-[5,5',6,6'-tetramethyl-3,3'-bis(1-methylethyl)[1,1'-biphenyl]-2,2'-diyl]/P,P,P',P'-tetrakis(2,4-dimethylphenyl) ester (compound of the formula (1)), to mixtures comprising this compound having a low chlorine content, and to metal complexes of this compound. This invention further relates to the use of the compound of the formula (1) and also of the metal complexes thereof as catalytically active composition in hydroformylation reactions and to the corresponding processes themselves.

The reactions between olefin compounds, carbon monoxide and hydrogen in the presence of a catalyst to give the aldehydes with one carbon atom more are known as hydroformylation or the oxo process. Catalysts used in these reactions are frequently compounds of the transition metals of group VIII of the Periodic Table of the Elements. Known ligands within these catalysts include, for example, compounds of the phosphine, phosphite and phosphonite classes each comprising trivalent phosphorus $P^{III}$. A good overview of the status of hydroformylation of olefins is found in R. Franke, D. Selent, A. Börner, "Applied Hydroformylation", Chem. Rev., 2012, DOI:10.1021/cr3001803.

The literature discloses the synthesis of symmetric bisphosphites, as disclosed in U.S. Pat. No. 4,789,498 for example, and the use thereof in catalytically active transition metal-containing compositions for the hydroformylation of unsaturated compounds.

In U.S. Pat. No. 4,769,498, and also in U.S. Pat. No. 5,723,641, preferably symmetric bisphosphites are prepared and used as ligands for hydroformylation. The symmetric bisphosphite ligands used in the hydroformylation are prepared at low temperatures. It is absolutely necessary to observe these low temperatures since higher temperatures, according to these US documents, would lead to rearrangements and ultimately to unsymmetric bisphosphites.

It has additionally been stated that symmetric ligands are more advantageous than the corresponding unsymmetric analogues.

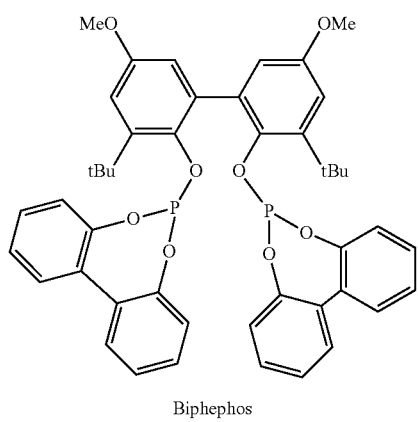

Biphephos

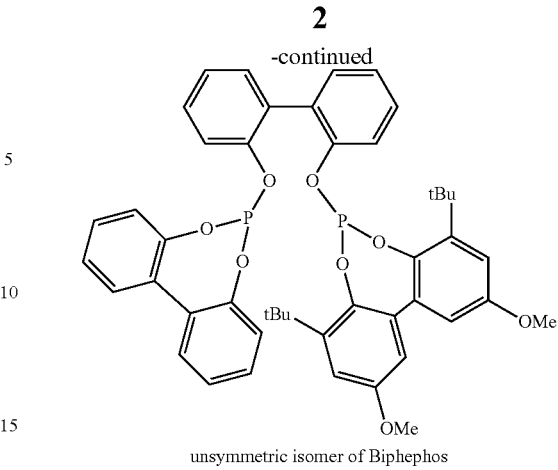

unsymmetric isomer of Biphephos

For example, Rhodium-catalyzed Hydroformylation, ed. by P. W. N. M. van Leeuwen and C. Claver, Kluwer Academic Publishers 2006, AA Dordrecht, NL, pages 45-46, table 2, presents the hydroformylation results for the two ligands depicted above under comparable conditions. In this context, it is clearly apparent that the symmetric Biphephos ligand (in the reference ligand 5a) features a much higher n/i selectivity and a higher activity than its unsymmetric isomer (in the reference ligand 7). In the hydroformylation reaction of propene, the symmetric ligand has an n/i selectivity of 53 and a reaction rate of 402, whereas the unsymmetric ligand has only an n/i selectivity of 1.2 and a reaction rate of 280. As shown by this comparison, the unsymmetric bisphosphites, when used as ligand in the transition metal-catalysed hydroformylation, thus have distinctly lower reactivities and lower n-regioselectivities than the corresponding symmetric compounds.

However, the above-depicted symmetric Biphephos ligand, owing to its many synthesis stages, especially in the phenol coupling, is very costly to prepare. Since the cost of the ligand has an essential effect on the overall economic viability of a process, it is desirable to find alternative ligands which have comparably good properties (yield and regioselectivity) but are less costly in terms of preparation.

The technical problem addressed by the invention is that of providing a symmetric ligand which, in the hydroformylation of unsaturated compounds, does not have the disadvantages detailed above from the prior art, but has one or more of the following properties:

1) a good activity/yield, 2) a high n-regioselectivity in relation to the hydroformylation, 3) a comparably inexpensive preparation.

The problem is solved by the preparation process proposed here for the compound of the formula (1) and the use thereof for catalysis in hydroformylation processes. The compound (1) is less expensive to prepare than the above-mentioned Biphephos ligand or the compound of the formula (3) substituted in a comparable manner to formula (1) (see comparative ligand in Example 2), and simultaneously has a very high n-regioselectivity in the hydroformylation and can be prepared in a high yield.

Compound of the formula (1):

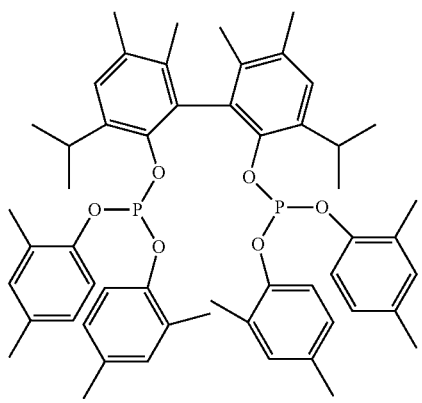

(1)

The present invention provides a complex comprising the compound of the formula (1) and a metal atom selected from Rh, Ru, Co and Ir. The compound of the formula (1) here is preferably the ligand in a ligand-metal complex.

The complex is preferably in a form corresponding to formula (2) in which the metal atom M is selected from Rh, Ru, Co and Ir.

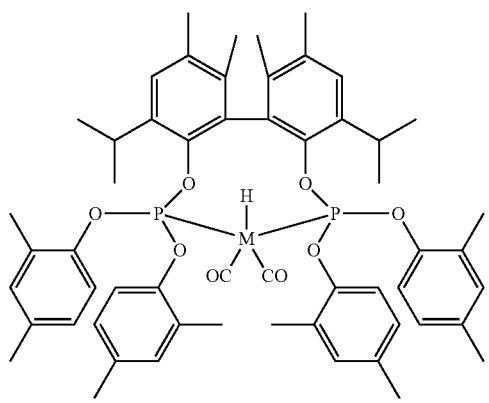

(2)

With particular preference, the metal atom is a rhodium atom.

The present invention additionally provides a process (hydroformylation process) comprising the process steps of:
a1) initially charging an olefin,
b1) adding
  a complex of the compound of the formula (1) with Rh, Ru, Co or Ir or a complex of the formula (2) or
  a compound of the formula (1) and a substance which provides a metal atom selected from Rh, Ru, Co and Ir,
c1) feeding in $H_2$ and CO,
d1) heating the reaction mixture, with conversion of the olefin to an aldehyde.

Process steps a1) to c1) can be effected here in any desired sequence.

In relation to the metal atom, it is possible to use an excess of compound of the formula (1) (ligand), and that not necessarily every ligand is bound in the form of a ligand-metal complex, but is present as "free ligand" in the reaction mixture.

The reaction is conducted under customary conditions. Preference is given to a temperature of 80° C. to 160° C. and a pressure of 1 to 300 bar.

Particular preference is given to a temperature of 100° C. to 160° C. and a pressure of 15 to 250 bar.

In a preferred embodiment, the metal is Rh.

The reactants for the hydroformylation in the process of the invention are olefins or mixtures of olefins, especially monoolefins having 2 to 24, preferably 3 to 16 and particularly preferably 3 to 12 carbon atoms, having terminal or internal C—C double bonds, for example 1-propene, 1-butene, 2-butene, 1- or 2-pentene, 2-methyl-1-butene, 2-methyl-2-butene, 3-methyl-1-butene, 1-, 2- or 3-hexene, the $C_6$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the $C_8$ olefin mixture obtained in the dimerization of butenes (di-n-butene, diisobutene), nonenes, 2- or 3-methyloctenes, the $C_9$ olefin mixture obtained in the trimerization of propene (tripropene), decenes, 2-ethyl-1-octene, dodecenes, the $C_{12}$ olefin mixture obtained in the tetramerization of propene or the trimerization of butenes (tetrapropene or tributene), tetradecenes, hexadecenes, the $C_{16}$ olefin mixture obtained in the tetramerization of butenes (tetrabutene), and olefin mixtures prepared by cooligomerization of olefins having different numbers of carbon atoms (preferably 2 to 4).

The olefins used may be unsubstituted or substituted. Suitable substituents are carboxyl groups, amino groups, carbonyl groups, halogens, especially chlorides, cyano groups and sulfo groups.

Preferred olefins are ethene, propene and butene, the term "olefin" also including olefin mixtures.

By means of the process according to the invention, preferably (isomeric) propenals, butanals, pentanals, nonanals or tridecanals, especially propenals or butanals, are prepared.

The process according to the invention using the ligands according to the invention can be used to hydroformylate α-olefins, terminally branched, internal and internally branched olefins.

Particular preference is given to a process comprising the process steps of:
a1) initially charging ethene, propene or butene,
b1) adding
  a complex of the compound of the formula (1) with Rh or a complex of the formula (2) with M=Rh or
  a compound of the formula (1) and a substance which provides a rhodium atom,
c1) feeding in $H_2$ and CO,
d1) heating the reaction mixture, with conversion of the olefin to an aldehyde,
wherein the process steps are run through in the sequence of a1, b1, c1, d1.

Particular preference is given to a process comprising the process steps of:
a1) initially charging 1-butene or 2-butene or mixtures comprising 1-butene and/or 2-butene,
b1) adding
  a complex of the compound of the formula (1) with Rh or a complex of the formula (2) with M=Rh or
  a compound of the formula (1) and a substance which provides a rhodium atom,
c1) feeding in $H_2$ and CO,
d1) heating the reaction mixture, with conversion of the olefin to an aldehyde, wherein the process steps are run through in the sequence of a1, b1, c1, d1.

The present invention further provides for the use of
- a compound of the formula (1) or
- a complex of the compound of the formula (1) with a metal cation selected from Rh, Ru, Co and Ir or
- a complex of the formula (2)

for catalysis in a hydroformylation process.

Preferably, the metal cation is rhodium.

With preference,
- the compound of the formula (1) or
- the complex of the compound of the formula (1) with a metal cation selected from Rh, Ru, Co and Ir or
- the complex of the formula (2)

is used for preparation of aldehydes having 3 to 20 carbon atoms by means of a hydroformylation process, especially for preparation of propenals, butanals, pentanals, nonanals or tridecanals by means of a hydroformylation process, and with particular preference for preparation of propenals or butanals by means of a hydroformylation process. In this context, the resulting aldehydes may be substituted or unsubstituted.

The present invention further provides a process for preparing a compound of the formula (1)

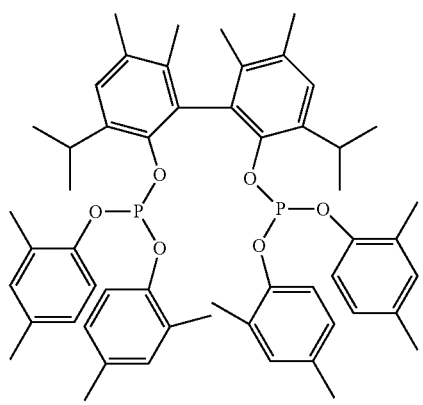

(1)

comprising the following process steps:
a2) preparing a formulation A2 comprising bis(2,4-dimethylphenyl) chlorophosphite in a first solvent,
b2) preparing a formulation B2 comprising 3,3'-diisopropyl-5,5',6,6'-tetramethyl-[1,1'-biphenyl]-2,2'-diol in a second solvent,
c2) mixing formulations A2 and B2 at a temperature between −50° C. and room temperature.

Preparation processes for the bis(2,4-dimethylphenyl) chlorophosphite and 3,3'-diisopropyl-5,5',6,6'-tetramethyl-[1,1'-biphenyl]-2,2'-diol reactants are described in the literature.

Independently of one another, the formulations A2 and B2 are preferably suspensions or solutions, especially solutions.

With preference, formulation B2 is metered into formulation A2. For this purpose, formulation A2, prior to the metered addition, is brought to a temperature between −50° C. and room temperature, preferably to a temperature between −40° C. and 10° C., further preferably to a temperature between −35° C. and 0° C., especially to a temperature between −25° C. and −10° C.

Bis(2,4-dimethylphenyl) chlorophosphite and 3,3'-diisopropyl-5,5',6,6'-tetramethyl-[1,1'-biphenyl]-2,2'-diol are preferably used in the process described above in a molar ratio between 4:1 and 1:1, more preferably between 3:1 and 1.3:1 and especially between 2.5:1 and 1.6:1.

The first and second solvents used may independently be aromatic hydrocarbons such as, more particularly, toluene, xylene, o-xylene, cresol; ethers such as, more particularly, tetrahydrofuran (THF), petroleum ether, diethyl ether, methyl tert-butyl ether (MTBE); nitriles such as, more particularly, acetonitrile (ACN); ethyl acetate; acetone; alcohols such as, more particularly, methanol, ethanol, isopropanol, butanol or mixtures of these solvents. With preference, nonpolar solvents are used.

In one embodiment of the process according to the invention, the first and second solvents are identical and are preferably toluene or xylene.

In another embodiment, the first and second solvents are different. For example, the first solvent is selected from ethyl acetate, anisole, ortho-xylene, toluene, acetone, methanol, ethanol, propanol, isopropanol, acetonitrile, and the second solvent is selected from ethyl acetate, anisole, ortho-xylene, toluene, acetone, methanol, ethanol, propanol, isopropanol, acetonitrile, tetrahydrofuran, diethyl ether, glycol, $C_5$-$C_{10}$-alkanes.

Preferably, the first solvent is toluene or xylene and the second solvent is acetonitrile or methanol or ethanol.

Preferably, one of the formulations A2 and B2 comprises an amine selected from triethylamine, dimethylaminobutane (DMAB), pentylamine, hexylamine, dibutylamine, N-methyl-2-pyrrolidone (NMP), triethanolamine, pyridine, dimethylaminopyridine (DMAP). Preferably, only formulation A2 comprises amine. Preference is given to using triethylamine or pyridine—preferably as a constituent of formulation A2.

Calculated relative to the 3,3'-diisopropyl-5,5',6,6'-tetramethyl-[1,1'-biphenyl]-2,2'-diol, preference is given to using 50 to 500 mol %, preferably 75 to 400 mol %, more preferably 100 to 300 mol %, of amine.

In a first particularly preferred embodiment, the process for preparing a compound of the formula (1)

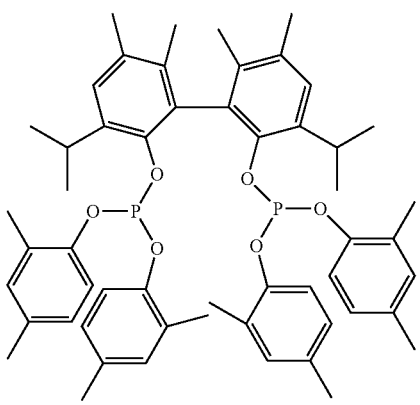

(1)

comprises the following process steps:
a2) preparing a suspension or solution A2 comprising bis(2,4-dimethylphenyl) chlorophosphite, an aromatic solvent, for example xylene, toluene or cresol, and optionally amine in an amount of 100-300 mol % (calculated relative to the 3,3'-diisopropyl-5,5', 6,6'-tetramethyl-[1,1'-biphenyl]-2,2'-diol in B2), b2) preparing a suspension or solution B2 comprising 3,3'-diisopropyl-5,5',6,6'-tetramethyl-[1,1'-biphenyl]-2,2'-diol and an aromatic solvent, for example xylene, toluene or cresol, c2) metering B2 into A2 stepwise, preferably continuously, wherein the molar ratio of bis(2,4-dimethylphenyl) chlorophosphite to 3,3'-diisopropyl-5,5',6,6'-tetramethyl-[1,1'-biphenyl]-2,2'-diol is between 3:1 and 1.3:1, especially between 2.5:1 and 1.6:1, and the suspension or solution A2, prior to the metered addition of B2, is brought to a temperature of −50° C., especially to a temperature of −30° C. to 0° C.

Preferably, in this case, the same solvent is used in steps a2 and b2.

In a further particularly preferred embodiment, the process for preparing a compound of the formula (1)

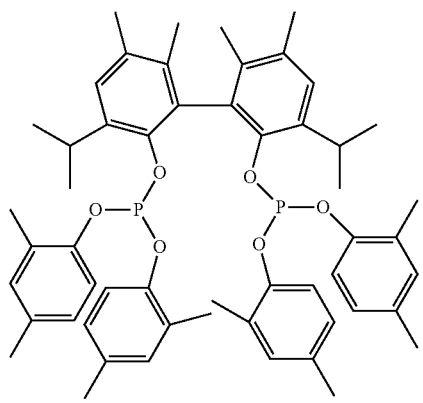

comprises the following process steps:

a2) preparing a suspension or solution A2 comprising bis(2,4-dimethylphenyl) chlorophosphite, toluene and optionally amine, preferably in an amount of 100-300 mol % (calculated relative to the 3,3'-diisopropyl-5,5', 6,6'-tetramethyl-[1,1'-biphenyl]-2,2'-diol in B2), b2) preparing a suspension or solution B2 comprising 3,3'-diisopropyl-5,5',6,6'-tetramethyl-[1,1',-biphenyl]-2,2'-diol and toluene, c2) metering B2 info A2 stepwise, preferably continuously, wherein the molar ratio of bis(2,4-dimethylphenyl) chlorophosphite to 3,3'-diisopropyl-5,5',6,6'-tetramethyl-[1,1'-biphenyl]-2,2'-diol is between 3:1 and 1.3:1, especially between 2.5:1 and 1.6:1, and the suspension or solution A2, prior to the metered addition of B2, is brought to a temperature of −30° C. to 0° C.

With preference, in the process according to the invention for preparing the compound of the formula (1) by the process steps described, a process step which serves to reduce the total chlorine content is conducted. The reduction in the total chlorine content preferably comprises the following steps:

i. dissolving the compound of the formula (1) in a first solvent or first solvent mixture at a temperature T between room temperature and the boiling point of the solution, preferably at at least 40° C., more preferably at at least 60° C. and especially at a temperature 2 to 15° C. below the boiling point of the solution;

ii. stirring the solution from step i);

iii. cooling the solution from step ii) by at least 10° C., preferably by 20° C. or at least 30° C., to form a suspension or emulsion;

iv. holding, preferably stirring, the suspension or emulsion from step iii) for 2 to 50 hours;

v. separating the phases of the suspension or emulsion from step iv).

Should no clear solution form here in step i), insoluble constituents are preferably removed and discarded.

The result is preferably a product comprising the compound of the formula (1) having a chlorine value of 10 ppm to 10 000 ppm, preferably of 20 ppm to 5000 ppm, further preferably 30 to 1000 ppm and especially below 500 or even below 300 ppm.

Accordingly, it is particularly preferable that the compound of the formula (1) or the complex of the compound of the formula (1) with a metal cation selected from Rh, Ru, Co and Ir or the complex of the formula (2)

has a chlorine value within the above-specified range and/or the compound of the formula (1) or the complex of the compound of the formula (1) with a metal cation selected from Rh, Ru, Co and Ir or the complex of the formula (2)

having a chlorine value within the above-specified range is used in the hydroformylation process according to the invention and/or is used in accordance with the invention for catalysis in a hydroformylation process.

The present invention accordingly further provides a mixture comprising the compound of the formula (1), characterized in that this mixture has a chlorine value—determined according to Wickbold—below 10 000 ppm, especially below 1000 ppm.

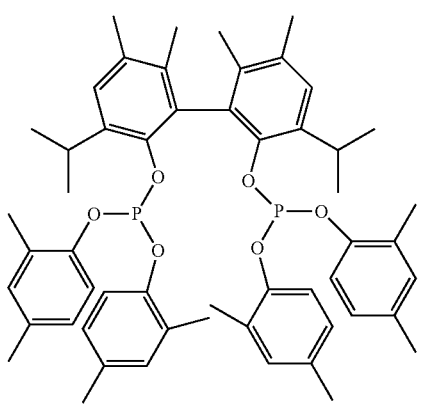

With preference, the chlorine value here is below 500 ppm, preferably below 400 ppm, more preferably below 300 ppm and further preferably below 200 ppm, where the chlorine value is based on weight.

This configuration of the invention described results from the fact that impurities in the form of chlorine compounds present difficulties: If the chlorine-containing contaminants get into a steel pressure reactor together with the organophosphorus compound used as ligand, the pressure reactor is subject to increased corrosion as a result of the chloride. This is especially true of continuous processes, in which the organophosphorus compounds are metered in over the course of the reaction. This is the case, for example, when the organophosphorus compound is used as a ligand in industrial scale hydroformylation. The metered addition inevitably also results in an accumulation of the secondary components in the reactor. This is particularly critical if chloride is one of the secondary components since chloride attacks even stainless steels: In the presence of chloride ions, there is a particular risk of stress-cracking corrosion, which can lead in more favourable cases to a premature shutdown of the process and to a reactor overhaul, but in less favourable cases even to rupture of the reactor. It is therefore of overriding importance to prevent entrainment of chlorine-containing compounds via the organophosphorus catalyst system.

The chloride content can be determined analytically in a simple manner, for example by aqueous titration. A more extensive determination is that of the total chlorine content, which, as well as the chlorides, also encompasses chlorine bound in other forms. Emphasis on the total chlorine content is also of material relevance, in that it cannot be ruled out that chlorine bound in other forms is also able to damage the reactor. In judging the limits for total chlorine, however, the chloride fraction remains crucial. A suitable method for determining the total chlorine content is the combustion according to Wickbold with sample preparation to DIN 51408 and analysis by ion chromatography to DIN EN ISO 10304. The chlorine values described in the context of this invention were determined according to Wickbold or by means of x-ray fluorescence analysis (XRF).

The invention is to be illustrated in greater detail hereinafter by working examples.

EXAMPLES

All the preparations which follow were carried out under protective gas using standard Schlenk techniques. The solvents were dried over suitable desiccants before use (Purification of Laboratory Chemicals, W. L F. Armarego (Author), Christina Chai (Author), Butterworth Heinemann (Elsevier), 6th edition, Oxford 2009). All preparative operations were effected in baked-out vessels. The products were characterized by means of NMR spectroscopy. Chemical shifts (δ) are reported in ppm. The $^{31}$P NMR signals were referenced as follows: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84). Nuclear resonance spectra were recorded on a Bruker Avance 300 or Bruker Avance 400.

Example 1: Reaction of bis(2,4-dimethlphenyl) chlorophosphite with 3,3'-diisopropyl-5,5',6,6'-tetramethyl-[1,1'-biphenyl]-2,2'-diol 8 g (0.020 mol) of bis(2,4-dimethylphenyl) chlorophosphite were dissolved at room temperature in 50 ml of toluene with addition of 3.9 ml (2.85 g, 0.028 mol) of triethylamine and equilibrated to −20° C. Added continuously to this solution within 12 minutes, while stirring, was a solution of 3.1 g (0.009 mol) of 3,3'-diisopropyl-5,5',6,6'-tetramethyl-[1,1'-biphenyl]-2,2'-diol in 50 ml of toluene. On completion of addition, the mixture was warmed to room temperature while stirring. Subsequently, the hydrochloride formed in the reaction was separated off by means of a quartz glass filter (frit) and the filtrate was concentrated to dryness at room temperature by means of oil-pump vacuum ($10^{-3}$ mbar). The resulting solids were stirred vigorously in 50 ml of acetonitrile for 1 h. After the phases had been separated, the upper phase was decanted off and the lower phase was dried at room temperature in an oil-pump vacuum ($10^{-3}$ mbar). According to $^1$H NMR, $^{31}$P NMR and $^{31}$P-$^1$H HMBC NMR (dissolved in toluene-$d_8$), the highly viscous residue contains 73.3% of compound of the formula (1). Chlorine value according to Wickbold: 58 ppm.

Example 2: Hydroformylation

In a 100 ml autoclave from Parr Instruments, 5.6 g of cis-2-butene were hydroformylated at 120° C. and synthesis gas pressure 20 bar (CO/$H_2$=1:1 (% by vol.)). As the precursor, Rh(acac)(CO)$_2$ was initially charged in 48.8 g of toluene. The ligand was used in a molar excess of 4:1 relative to rhodium. As the ligand, 0.0779 g of ligand was used in the catalyst mixture solution. Tinuvin 770DF was used as stabilizer in a molar ratio to the ligand of about 1:1. In addition, a GC standard was added. About 6 g of reactant were metered in after the reaction temperature envisaged had been attained.

During the reaction, the pressure was kept constant via synthesis gas regulation with a mass flow meter. The stirrer speed was 1200 min$^{-1}$. Samples were taken from the reaction mixture after 12 hours.

In addition, the compound (3) was tested under corresponding conditions. Compound (3) was prepared according to EP 2 907 819 A1.

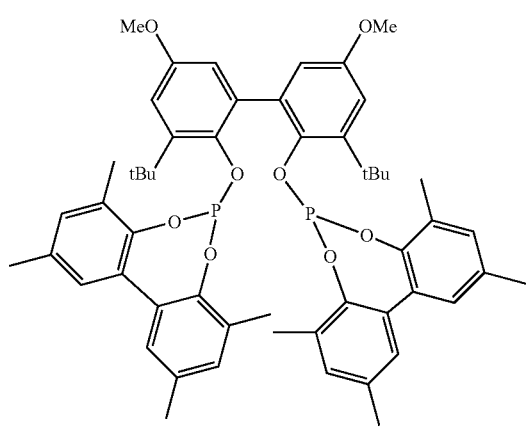

(3)

Table 1 shows the results of hydroformylation of cis-2-butene at synthesis gas pressure 20 bar.

TABLE 1

| Ligand = compound (X) X = | Aldehyde yield in [%] | n-Pentanal regioselectivity in % |
|---|---|---|
| 1* | 79 | 98 |
| 3 | 66 | 90 |

*inventive compound of the formula (1)

Definition of the Selectivity:

In the hydroformylation, there is the n/iso selectivity (n/iso=the ratio of linear aldehyde (=n) to branched (=iso)

aldehyde)). The n-pentanol regioselectivity here means that this amount of linear product was formed. The remaining percentage then corresponds to the branched isomer. The selectivity rate was determined by means of area comparison in the GC.

The results show that the compound (1) in the hydroformylation both enables a higher yield, i.e. is more reactive, and features a higher regioselectivity with regard to the n/iso ratio than the compound (3).

The invention claimed is:

1. A symmetric bidentate metal ligand complex mixture comprising a compound represented by formula (2):

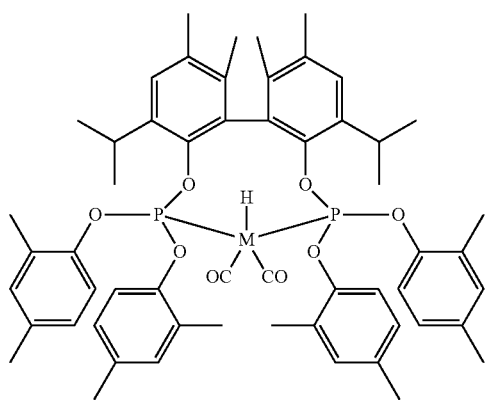

(2)

and a metal atom selected from the group consisting of Rh, Ru, Co and Ir, wherein the symmetric bidentate metal ligand complex mixture has a chlorine value according to Wickhold below 10,000 ppm.

2. The bidentate metal ligand complex mixture according to claim 1, wherein M is Rh.

3. A process for converting an olefin to an aldehyde comprising the process steps of:
   a1) initially charging an olefin having 2 to 24 carbon atoms,
   b1) adding
      the symmetric bidentate metal ligand complex mixture according to claim 1,
   c1) feeding in $H_2$ and CO,
   d1) heating the reaction mixture, with conversion of the olefin to an aldehyde.

4. The process according to claim 3, characterized in that the metal atom is Rh.

5. The process according to claim 3, wherein the olefin having 2 to 24 carbon atoms is selected from ethene, propene butene, 1-butene or 2-butene.

6. The process according to claim 3, characterized in that, in step a1), wherein the olefin having 2 to 24 carbon atoms is selected from 1-butene or 2-butene.

7. A catalytic hydroformylation process comprising contacting an olefin with
   the symmetric bidentate metal ligand complex mixture according to claim 1.

8. The process according to claim 7, wherein the hydroformylation process converts the olefin to substituted or unsubstituted aldehydes having 3 to 20 carbon atoms, including substituted or unsubstituted propenals, butanals, pentanals, nonanals, tridecanals, substituted or unsubstituted propenals, butanals or pentanals.

9. The process according to claim 7, wherein the substituted or unsubstituted aldehydes having 3 to 20 carbon atoms include substituted or unsubstituted propenals, butanals or pentanals.

* * * * *